US011355221B2

(12) United States Patent
Mansouri

(10) Patent No.: US 11,355,221 B2
(45) Date of Patent: Jun. 7, 2022

(54) CLASSIFICATION SYSTEMS, AND METHODS OF COLLECTING, ASSOCIATING, STORING, SEARCHING, AND PROVIDING HEALTHCARE INFORMATION, AND CONNECTING HEALTHCARE PARTICIPANTS GLOBALLY

(71) Applicant: Mahdis Mansouri, Washington, DC (US)

(72) Inventor: Mahdis Mansouri, Washington, DC (US)

( * ) Notice: Subject to any disclaimer, the term of this patent is extended or adjusted under 35 U.S.C. 154(b) by 553 days.

(21) Appl. No.: 15/725,214

(22) Filed: Oct. 4, 2017

(65) Prior Publication Data

US 2018/0196923 A1 Jul. 12, 2018

Related U.S. Application Data

(60) Provisional application No. 62/443,844, filed on Jan. 9, 2017.

(51) Int. Cl.
*G16H 10/60* (2018.01)
*G16H 10/20* (2018.01)
*G16H 50/20* (2018.01)
*G16H 50/70* (2018.01)
*G06F 16/903* (2019.01)

(52) U.S. Cl.
CPC ....... *G16H 10/60* (2018.01); *G06F 16/90335* (2019.01); *G16H 10/20* (2018.01); *G16H 50/20* (2018.01); *G16H 50/70* (2018.01)

(58) Field of Classification Search
CPC . G06F 19/362; G06F 16/90335; G16H 10/60; G16H 50/70; G16H 50/20; G16H 10/20
USPC ............................................................ 705/2
See application file for complete search history.

(56) References Cited

U.S. PATENT DOCUMENTS

| | | | | |
|---|---|---|---|---|
| 5,583,758 A * | 12/1996 | McIlroy | ............... | G06F 19/325 705/2 |
| 6,055,494 A * | 4/2000 | Friedman | ............... | G06F 40/35 704/9 |
| 6,088,677 A | 7/2000 | Spurgeon | | |
| 6,658,431 B1 | 12/2003 | Norman | | |
| 6,915,254 B1 * | 7/2005 | Heinze | ................... | G06F 40/20 704/9 |
| 7,383,197 B1 | 6/2008 | Neuman | | |
| 7,437,302 B2 * | 10/2008 | Haskell | ................ | G06F 19/325 705/2 |

(Continued)

*Primary Examiner* — Michael Tomaszewski
*Assistant Examiner* — Rachael Sojin Stone
(74) *Attorney, Agent, or Firm* — The Roy Gross Law Firm, LLC; Roy Gross

(57) ABSTRACT

A method and system of associating globally and nationally recognized health and healthcare classification systems with their respective common terms, to create user-friendly classification systems. Users can suggest common terms to be added to the classification system codes. A method of storing and retrieving healthcare information including storing healthcare information for a plurality of members in a database; associating one or more classification system codes and one or more profiles with the stored healthcare information; and retrieving the stored healthcare information from the database in response to pre-defined and/or user-defined search input.

15 Claims, 8 Drawing Sheets

(56) References Cited

U.S. PATENT DOCUMENTS

| | | | | |
|---|---|---|---|---|
| 7,533,030 | B2* | 5/2009 | Hasan | G06Q 30/04 |
| | | | | 705/2 |
| 7,610,192 | B1* | 10/2009 | Jamieson | G06Q 40/08 |
| | | | | 704/9 |
| 7,650,327 | B2* | 1/2010 | Remsen | G06F 16/9558 |
| | | | | 707/737 |
| 7,752,060 | B2 | 7/2010 | Hicks et al. | |
| 7,853,446 | B2* | 12/2010 | Allard | G16H 10/60 |
| | | | | 704/9 |
| 8,949,940 | B1* | 2/2015 | Shenoy | G06Q 10/10 |
| | | | | 707/636 |
| 10,319,004 | B2* | 6/2019 | Reiser | G06Q 10/00 |
| 2003/0078911 | A1* | 4/2003 | Haskell | G06F 19/324 |
| 2006/0026037 | A1 | 2/2006 | Lubbert | |
| 2007/0061393 | A1* | 3/2007 | Moore | G06F 19/325 |
| | | | | 709/201 |
| 2010/0049703 | A1* | 2/2010 | Colera | G06F 16/345 |
| | | | | 707/603 |
| 2014/0122117 | A1* | 5/2014 | Masarie, Jr. | G06Q 50/22 |
| | | | | 705/3 |
| 2015/0379241 | A1* | 12/2015 | Furst | G06F 40/247 |
| | | | | 705/3 |
| 2016/0132643 | A1* | 5/2016 | Radhakrishna | G16H 70/40 |
| | | | | 705/3 |
| 2016/0283673 | A1* | 9/2016 | Charlot | G06F 16/24573 |
| 2017/0262604 | A1* | 9/2017 | Francois | G06F 19/3418 |
| 2018/0011922 | A1* | 1/2018 | Sethumadhavan | G06Q 10/04 |
| 2018/0046764 | A1* | 2/2018 | Katwala | G06F 40/169 |
| 2018/0075192 | A1* | 3/2018 | Sethumadhavan | G06F 16/21 |

* cited by examiner

CLASSIFICATION SYSTEMS, AND METHODS OF COLLECTING, ASSOCIATING, STORING, SEARCHING, AND PROVIDING HEALTHCARE INFORMATION, AND CONNECTING HEALTHCARE PARTICIPANTS GLOBALLY

CROSS REFERENCE TO RELATED APPLICATIONS

The present invention claims priority to U.S. Provisional Patent Application No. 62/443,844 filed on Jan. 9, 2017 entitled "INTERNET SYSTEMS AND METHODS OF COLLECTING, STORING, SEARCHING, PROVIDING AND CREATING HEALTHCARE INFORMATION, AND CONNECTING HEALTHCARE SYSTEMS GLOBALLY." The contents of this application are incorporated by reference into this application in its entirety.

FIELD OF THE INVENTION

The present invention relates to methods and systems for collecting, associating, searching and providing medical and healthcare information. More specifically, the present invention relates to creating and using novel health and medical classification systems that are user-friendly for both medical professionals and non-professionals to access medical and healthcare information and all forms of related academic and business services and product information for various medical related topics. This system does so by associating current medical classification systems with their more commonly used terms, and associating those user-friendly classification codes with medical and healthcare information to provide a dynamic system for searching and retrieving local and global medical and healthcare information, as well as information for their related academic and business services and products for all users.

BACKGROUND OF THE INVENTION

Conventional online-based platforms for healthcare information are generally restricted to generic searches for only a single aspect of healthcare information. These platforms may use generic medical terminology in order to encourage non-medical professional users to use their platform. This type of simplification will result in a loss of search specificity, which is often required when searching for health-related information, medical providers, and other health services and products. However, using medical terminology and universal classification systems that are accepted and used within the health/medical industry would mean that a majority of users are excluded from being able to use the platform. In addition to reduced specificity with respect to search results and exclusions of non-medical professional users, these limitations do not allow sites to transcend cultural and/or language barriers where the generic terms may be different.

Most sites generally only allow a user to search by signs/symptoms of an illness and/or healthcare providers' specialties. In addition, conventional sites mostly provide healthcare information for self-diagnosis and diagnosed conditions, as well as capabilities for finding providers. For example, a consumer searching for information related to diseases, signs and symptoms, abnormal findings, treatments, social circumstances, and external causes of injury or diseases must search a number of web sources via a trial-and-error approach to obtain the desired information. Beyond information relating to diseases—for example, information relating to employment, recent research, and/or healthcare policies—a consumer would need to search even more web sources via the trial-and-error approach. This is time consuming and difficult. Users often do not have the resources or the energy to search all required websites for all their required medical and healthcare information.

In addition, no platforms provide direct communication between various stakeholders across different sectors of healthcare. Rather, conventional online-based platforms for healthcare information only permit unilateral communication of information. For example, a web source may communicate information to a consumer, but a consumer may not be able to communicate with the web source. Moreover, it is not possible for healthcare participants to connect with developers of healthcare products of rare diseases for further discussion. While some platforms may permit bilateral communication of information (e.g., from web source to consumer and from consumer to web source), these platforms are precluded from providing relevant healthcare information to all healthcare participants because the scope of their content is limited to a few aspects of healthcare information.

Existing known systems that have some aspects that may be considered closest to the described invention include the following: U.S. Pat. No. 6,088,677 to Spurgeon; U.S. Pat. No. 6,658,431 to Norman, Jr.; U.S. Pat. No. 7,383,197 to Neuman; U.S. Pat. No. 7,752,060 to Hicks et al.; and US 2006/0026037 to Lubbert.

Disadvantageously however, all known systems fail to provide a global, inclusive and easy to use comprehensive online-based platform that captures all aspects of healthcare and makes them available to all users in an easy to use manner that is based on the structure of health and medical classification systems, associated with the more commonly used terms, to provide for an easy to use flow of medical and healthcare related information.

Thus, it is desired to provide such a system and method that solves the disadvantages in the prior art.

SUMMARY OF THE INVENTION

It is an object of the present invention to provide a comprehensive online-based platform for all aspects of healthcare and to provide medical and healthcare information.

It is an object of the present invention to provide a method system that connects generic (medical) terms with their respective formally used terms.

It is an object of the present invention to provide a method and system having each term/code within a formal classification system, used globally and nationally, concatenated with their generic terms. This would allow any internet user, regardless of their familiarity with medical terminology to search with as much specificity as needed, or with as much a specificity as they were able and the formal medical term would be presented to them.

It is another object of the invention to allow users of this platform to suggest modifications to the classification systems by adding additional generic terms to the classification system codes, further ensuring the nuances that come with geographical location are not a barrier to search specificity.

It is another object of the invention to review suggested additions of generic terms to the classification system codes and allow them to be added to the code for all website users.

It is another object of the invention for this platform may also allow all fields within the health/medical industry to be accessible via a single source for any healthcare participant, and presents opportunities for communicating beyond conventional platforms.

These and other objects of the invention are achieved by providing a method of collecting, associating, storing, searching, and retrieving healthcare information, comprising: providing a database and a processor; collecting and storing, via said processor, healthcare information on said database, wherein said healthcare information includes one or more classification system codes and one or more member profiles, which identifies a member submitting healthcare information by their expertise within the industry; correlating, via said processor, one or more common condition terms with one or more classification system codes, wherein the correlation between the common condition terms and the one or more classification system codes allows said healthcare information collected from one or member profiles to be retrieved; and retrieving, via said processor, said stored healthcare information from said database in response to user-defined inputs that may include the one or more common or formal terms.

In certain embodiments, one or more common condition terms are associated with formal terms, and with one or more profiles with said stored healthcare information.

In certain embodiments, the collected and stored healthcare information includes information relating to one or more of diseases, conditions, symptoms, abnormal findings, treatments, complaints, social circumstances, and external causes of injuries and/or diseases.

In certain embodiments, each of the members input the stored healthcare information via a profile specific questionnaire.

In certain embodiments, the profiles include one or more of consumers, providers, insurers, policy and regulatory, products and devices, services and solutions, advocacy and philanthropy, research, education, and employment.

In certain embodiments, the formal classification system codes include the ICD-10 Clinical Modifications, other World Health Organizations classification systems and any adaptations thereof.

In certain embodiments, the classification system codes are updated based on the latest version of the globally and/or nationally recognized system codes they are based on.

In certain embodiments, the classification system codes are globally and/or nationally recognized classification system concatenated with their common terms.

In certain embodiments, common terms can be suggested by users, and subsequently added once approved. In certain embodiments, common terms can be added by a user either immediately or upon approval.

In certain embodiments, the classification system code is generated in response to a user-defined input. In certain embodiments, search results are generated in response to user-defined inputs.

In certain embodiments, the user-defined input includes one or more of classification system codes, profiles, keywords, and area codes.

In certain embodiments, the method further comprises directing the user to one or more member websites.

In certain embodiments, the method further comprises facilitating communications between users and members.

In certain embodiments, the classification system codes are World Health Organization (WHO) classification codes.

In certain embodiments, the results of concatenating formal classification system codes with their generic/common terms include using Health™ classification codes.

In certain embodiments, one or more Health™ classification system codes are based on globally and/or nationally recognized health and medical classification systems Other objects of the invention are achieved by providing a system for collecting, storing, associating, searching, and retrieving healthcare information, comprising: a database storing healthcare information, wherein healthcare information includes one or more classification system codes and one or more member profiles identifying a member submitting healthcare information; at least one processor; software executing on the processor configured to control access of said healthcare information; said software is configured to correlate one or more common condition terms with one or more classification system codes, wherein the correlation between the common condition terms and the one or more classification system codes allows said healthcare information collected from one or member profiles to be retrieved; and said software is configured to retrieve the stored healthcare information from the database in response to user-defined inputs that include the one or more classification system codes.

Other objects of the invention are achieved by providing a method of collecting, associating, storing, searching, and retrieving healthcare information, comprising: providing a database and a processor; collecting and storing, via said processor, healthcare information on said database, wherein said healthcare information includes one or more classification system codes; correlating, via said processor, one or more common condition terms with one or more classification system codes, wherein the correlation between the common condition terms and the one or more classification system codes allows said healthcare information to be retrieved from said database; and retrieving, via said processor, said stored healthcare information from said database in response to user-defined inputs that include the one or more common condition terms.

Other objects of the invention and its particular features and advantages will become more apparent from consideration of the following drawings and accompanying detailed description. It should be understood that the detailed description and specific examples, while indicating the preferred embodiment of the invention, are intended for purposes of illustration only and are not intended to limit the scope of the invention.

BRIEF DESCRIPTION OF THE DRAWINGS

This written disclosure describes illustrative embodiments that are non-limiting and non-exhaustive. In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

Reference is made to illustrative embodiments that are depicted in the figures, in which.

DETAILED DESCRIPTION OF THE INVENTION

Figure 1:
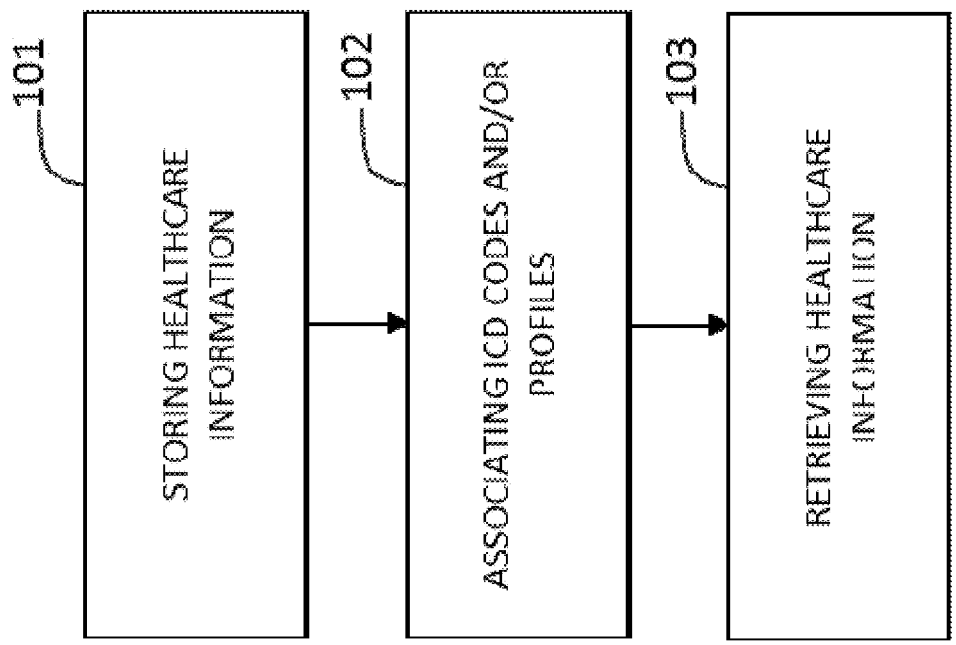
FIG. 1 is a flowchart of a method of providing healthcare information, according to one or more embodiments of the present disclosure.

In the following description, numerous details are set forth for the purpose of explanation. However, one of ordinary skill in the art will realize that the invention may be practiced without the use of these specific details.

The invention of the present disclosure is directed to creating a classification system using methods of concatenating globally and nationally accepted classification systems, by each individual term/code, with their respective generic terms. The novel systems resulting from concatenating formal health and medical codes with their generic terms are include associating the respective generic terms with Healith' classification system codes.

In certain embodiments, the invention of the present disclosure includes system and methods of collecting, associating, storing, searching, providing, and communicating healthcare information tied to codes available on an internet website, server, memory and or processor.

In certain embodiments, the invention of the present disclosure is related to systems and methods of allowing, facilitating and promoting communication between healthcare participants.

In certain embodiments, the invention of the present disclosure relates to a centralized repository of stored healthcare information accessible via a single access point (e.g., website) from which healthcare participants may submit any type of medical, health related and/or healthcare information, and anyone may search for and retrieve that information. All information in this repository is submitted by and collected from healthcare participants (e.g., members) through a structured process that first ties the information to classification code (such as classification codes and systems developed by the WHO, CMS, etc. as well as modified or hybrid classification codes such as Healith™ classification codes) selected by the healthcare participant, then a profile. Profiles may be tailored to specific healthcare participants, including, but not limited to, consumers, providers, insurers, policy and regulatory, products and devices, services and solutions, advocacy and philanthropy, research, education, and employment. Participants searching for healthcare information (e.g., users) may select one or more initial search inputs (search signals) that includes the classification codes (Healith™, WHO classification systems, CMS classification system), symptoms, and treatments.

Users then select one or more profiles per search to find specific healthcare information and retrieve this information with unprecedented precision. The system learns patterns (as it includes heuristic learning) as it is used and suggests codes for searching.

In certain embodiments, the system and method promotes members (healthcare participants who have provided information in the system) to users. The system also monitors quality of data input by members.

In certain embodiments, healthcare participants, for example, may connect directly through the system in various ways. For example, healthcare participants may use the system to message other healthcare participants who meet specified criteria, which may be selected. In this manner, the invention of the present disclosure provides a comprehensive global platform for communication and information finding for all healthcare participants. A feature that is called Healith™ Direct. There is also Healith™ Notifications which allows members to select criteria and be notified when matching information is submitted by a member.

In certain embodiments, the invention of the present disclosure is related to implementing a structured messaging system to allow members to communicate with a site developer regarding addition/change requests to the questionnaire lists. This will help meet the changing needs of users and members by ensuring they are able to accurately and topically represent their services.

In certain embodiments, the invention of the present disclosure provides access to all aspects related to diseases, conditions, diagnosis, symptoms, treatments, external factors, and functional measurements, and allows connections across these aspects globally. Information is comparable from different sources and available through convenient and flexible queries. This offers a platform for healthcare participants to channel developments, research, opinion, available careers, and other medical and healthcare related information.

In certain embodiments, the invention of the present disclosure relates to creating a classification system (and classification codes) using methods of concatenating globally and nationally accepted medical classification systems, by each individual term/code, with their respective generic terms.

In certain embodiments, the classification system and classification codes may use globally accepted classification systems created by the World Health Organization (WHO) and nationally accepted classification systems created by nation states. For example, Current Procedural Terminology (CPT) classification system created are used within the U.S. These established systems, used within the healthcare industry, may be modified and/or combined with their generic terms.

In certain embodiments, the invention of the present disclosure includes methods of providing healthcare information comprising storing healthcare information for a plurality of members in a database, associating one or more codes and one or more profiles with the stored healthcare information, and retrieving the stored healthcare information from the database in response to a plurality of signals.

In certain embodiments, the invention of the present disclosure includes a unique health related classification system for connecting healthcare participants. The system combines the formal (medical) terminology of diseases, diagnosis, conditions, external factors, functional measurements and/or procedures with their more commonly used terms.

In certain embodiments, the method and system connects common terms with medical related terms in formal systems (for example, ICDs).

In certain embodiments, members and users of the system and platform are able to add additional common terms so anyone can search from any part of the world by whatever reference to the medical diagnosis they are familiar with.

In certain embodiments, the method and system includes methods of associating classification codes to healthcare related information provided by users, i.e. anyone who interacts with the system, for the purposes of information collecting, associating, storing, searching, retrieving, and communication at a global level.

In certain embodiments, users submitting healthcare information on the system are provided with one or more profiles identifying the user submitting the information, wherein profiles include one or more of consumers, providers, insurers, policy and regulatory, products and devices, services and solutions, advocacy and philanthropy, research, education, and employment In certain embodiments, users submitting healthcare information submit common condition terms to be associated with one or more classification codes, wherein a search submitted by a user that includes common condition terms returns submitted healthcare information having one or more classification codes associated with the submitted common condition terms.

In certain embodiments, the method includes allowing association of classification system codes and users' information are done by user self-selected profile(s) questionnaire(s) and are stored in a database.

In certain embodiments, the method includes searching for the stored healthcare information using codes and any user defined keyword(s) and search strings submitted as part of profile creation.

In certain embodiments, the method includes the collected and stored healthcare information including information relating to one or more of diseases, conditions, symptoms, abnormal findings, complaints, social circumstances, and external causes of injuries and/or diseases.

In certain embodiments, the method includes the classification system codes include the ICD-10 Clinical Modifications and any adaptations thereof.

In certain embodiments, the method includes automatically updating the classification system codes.

In certain embodiments, the method includes generating a classification system code in response to a user-defined input.

In certain embodiments, the method includes directing the user to one or more information provider websites.

Healith™ System

In certain embodiments, the invention of the present disclosure is related to protecting the Healith™ classification systems http://www.healith.com/. The nomenclature of the Healith™ classification systems includes common term (formal term) medical terminology. The same common term can be associated with multiple medical terms. Each formal medical term may have one or more associated common terms, which may be separated by a comma or other special character.

For example, for pink eye, there are several ICDs for pink eye depending on which eye, acuity, etc. The medical diagnosis is bacterial conjunctivitis.

In Healith™, the nomenclature is (Pink eye) Bacterial conjunctivitis. Each type of bacterial conjunctivitis would have (pink eye) concatenated. If a user refers to it as something else they can request to have a common term added, which may then be separated by a comma from Pink Eye within the parenthesis containing all common terms.

The advantage of being able to dynamically add terms allows a user to get into more serious diagnosis such as cancer. Oncologists, for example, treat different forms of lung cancer which are distinguishable by their formal medical diagnosis code.

The Healith system allows members to submit the user's information and associate themselves with a specific Healith classification system code. Allowing users to then search for lung cancer, of the specific diagnosis and find the appropriate providers, information, policies, medical devices, etc.

The Healith™ classification system codes are the backbone of how Healith™ connects healthcare participants. Moreover, Healith™ involves a user questionnaire and users submitting their information to Healith™ go through a questionnaire process.

Definitions

The terms recited below have been defined as described below. All other terms and phrases in this disclosure shall be construed according to their ordinary meaning as understood by one of skill in the art.

As used herein, "member(s)" may refer to any individual, entity, and/or healthcare participant who provides healthcare information (e.g., information organized and stored in the centralized repository) and "user(s)" may refer to any individual, entity, and/or healthcare participant who searches for healthcare information As used herein, "healthcare information" refers to any healthcare information and any healthcare-related information, including member information.

As used herein, "healthcare participants" refers to any individual and/or entity, including, but not limited to members and users. For example, in some embodiments, healthcare participants may include one or more of individuals representing their own interests and/or needs, individuals representing the interests and/or needs of an organization as employees/owners, individuals representing needs and/or interests of another group of individuals, etc. The interests and/or needs may be anything related to healthcare. For example, where conventional sites provide information limited to individuals looking for symptom information and providers that treat those symptoms, the healthcare participants of the present disclosure may include anyone looking for anything related to healthcare.

As used herein, "ICD" and/or "ICD code(s)" refer to diagnostic codes for classifying healthcare information and healthcare-related information, including, but not limited to any previous, current, and/or future version of one or more of the International Statistical Classification of Diseases and Related Health Problems and the International Classification of Diseases. For example, it may include ICD-1, ICD-2, ICD-3, ICD-4, ICD-5, ICD-6, ICD-7, ICD-8A, ICD-9, and ICD-10. It may include modifications such as the International Classification of Diseases, Clinical Modification, such as, ICD-9-CM, ICD-10-CM, and ICD-10-CA.

As used herein, Healith™ classification code is a proprietary classification system where the commonly used term for a medical condition is combined with the formal medical terminology (ex. ICDs) used within the industry for diagnosis and billing.

Embodiments of the present disclosure include methods of searching for and retrieving healthcare information. In particular, a user may search for and retrieve healthcare information by selecting one or more Healith™ Code, WHO classification system codes, CMS classification system codes, symptoms and treatments. The selection of one or more Healith™ classification codes, and/or one or more profiles in searching for healthcare information produces results with greater specificity and precision. For example, in some embodiments, a user may select a Healith™ classification system and a profile to narrow the scope of the search. Alternatively, in other embodiments, a user may also conduct a keyword search after the profile selection to narrow the scope of the search even further.

In some embodiments, the user interface may be developed with Java and implemented with AJAX and PHP while the database storing the information may be developed and MySQL. In some embodiments, the database storing the information may be developing using blockchain technology.

A user may search for and retrieve healthcare information by selecting one or more Healith™ classification codes. These may be WHO classification system codes and national classification system codes, concatenated with their more commonly used terms The WHO classification system codes may include International Classification of Diseases (ICD) codes and/or International Classification of Functioning, Disability and Health (ICF) codes. The ICD is a globally recognized and accepted standardized diagnostic tool for epidemiology, health management, and clinical purposes. It includes healthcare information, such as, information on diseases, signs and symptoms, abnormal findings, complaints, social circumstances, and external causes of injury or diseases. It may be utilized for analysis of the general health situation of population groups and for monitoring incidence and prevalence of the general health situation in various countries. The ICD may be utilized by physicians, nurses, providers, researchers, managers, information technology workers, policymakers, insurers, and patient organizations to classify diseases and other healthcare information and to generate reports thereon. Since its inception in about 1948, the WHO periodically revises and publishes updated versions of the ICD. It is accepted and used by all WHO member states. In many embodiments, "ICD" refers to ICD-10-CM. The ICD-10-CM is a modification of the WHO-based ICD published by the United States. The ICD-10-CM categorized diseases into 21 chapters and includes more detail than the WHO-based ICD. Table 1 below lists the 21 chapters of the ICD-10-CM.

TABLE 1

List of Chapters of ICD-10 Clinical Modification

| | |
|---|---|
| I | Certain infections and parasitic diseases (A00-B99) |
| II | Neoplasms (C00-D49) |
| III | Diseases of the blood and blood-forming organs and certain disorders involving the immune mechanism (D50-D89) |
| IV | Endocrine, nutritional and metabolic diseases (E00-E90) |
| V | Mental and behavioral disorders (F01-F99) |
| VI | Diseases of the nervous system (G00-G99) |
| VII | Diseases of the eye and adnexa (H00-H59) |
| VIII | Diseases of the ear and mastoid process (H60-H95) |
| IX | Diseases of the circulatory system (I00-I99) |
| X | Diseases of the respiratory system (J00-J99) |
| XI | Diseases of the digestive system (K00-K93) |
| XII | Diseases of the skin and subcutaneous tissue (L00-L99) |
| XIII | Diseases of the musculoskeletal system and connective tissue (M00-M99) |
| XIV | Diseases of the genitourinary system (N00-N99) |
| XV | Pregnancy, childbirth and the puerperiu (O00-O99) |
| XVI | Certain conditions originating in the perinatal period (P00-P96) |
| XVII | Congenital malformations, deformations and chromosomal abnormalities (Q00-Q99) |
| XVIII | Symptoms, signs and abnormal clinical and laboratory findings, not elsewhere classified (R00-R99) |
| XIX | Injury, poisoning and certain other consequences of external causes (S00-T98) |
| XX | External causes of morbidity (V01-Y99) |
| XXI | Factors influencing health status and contact with health services (Z00-Z99) |

The 21 chapters include various tiers of subchapters within each chapter. Each chapter and all their tiers of subchapters have first been manipulated so each code can be used in the Healith™ System, and then concatenated with their associated common terms. In many embodiments, a user may select one or more chapters and/or subchapters in searching for healthcare information to improve the specificity and precision of the results.

ICF codes function similarly to ICD codes. ICF is a classification of health and health-related domains. As the functioning and disability of an individual occurs in a context, ICF also provides a list of environmental factors. ICF is the WHO framework for measuring health and disability at both individual and population levels. All 191 WHO Member States have officially endorsed the ICF as the standard to describe and measure health disability.

A user may search for and retrieve healthcare information by selecting one or more profiles. In general, the profiles provide another layer of specificity (e.g., filter) in searching for healthcare information. A profile may be provided for any type of healthcare participant. For example, the profiles may include, but are not limited to, one or more of consumers, providers, insurers, policy and regulatory, products and devices, services and solutions, advocacy and philanthropy, research, education, and employment. The profiles provide a framework within which the invention of the present disclosure provides opportunities for different users (e.g., consumers to providers, providers to consumers, researchers to consultants, app developers to investors, consumers to consumers, advocates to insurance companies, policymakers to providers, etc.) to communicate.

In one embodiment, a user first views a list of all available Healith™ classification systems, symptoms, and treatments. For example, 21 expandable Healith™ Code chapters listed with a description in the same order and hierarchy as the formal classification system it's built from but combined with their common terms. Upon selecting the desired search category. The user next views a list of Healith™ Profiles. The search category information may be queued to populate within each of the Healith™ profiles. In some embodiments, a user may be presented with an option to further narrow search results by entering one or more keywords, selecting one or more keywords from a Healith™ profile specific list, and/or entering one or more zip codes. For example, in some embodiments, a user may select one or more keywords by selecting from a list of pre-drafted keywords or by manually entering in a desired keyword(s). The list of selectable keywords may be profile specific. Entering keywords and/or zip codes is optional. Upon selecting one or more profiles and entering in keywords and/or zip codes, if any, the user subsequently reviews the results of the search. The results may be sorted by predetermined profile-specific information of members. In some embodiments, Healith classification systems may be suggested based on additional searches by other users searching for that same Healith™ classification systems.

In some embodiments, the search results include information from specific fields of the profile questionnaires provided by the member, including a hyperlink to connect users directly to a member's website. In addition, a social networking platform may be provided to permit users to directly connect with other users and members. In some embodiments, users may directly message other users and members through the website, allowing their private information to be protected. In addition, members may submit blog posts, and others may respond to posts or participate in real-time question-and-answer events or in real-time polls (e.g., facilitating instant chatting). The site may also allow users to specify message criteria by selecting search category system codes, profile, and keywords of interest to communicate to members with profiles matching the criteria (this feature is called Healith™ Direct). A free text section may be included in some embodiments. Members with matching criteria may receive a message through the platform from a user that may be directly responded to. This allows targeted connection between healthcare participants. In this way, the invention of the present disclosure creates an opportunity for members to connect with other consumers, providers, insurance companies and payors, policy and regulatory organizations, product and device manufacturers, service- and solution-focused organizations, advocates, researchers, educators, and potential employers via a single website with the benefit of the specificity of globally recognized and accepted classification codes, which may be concatenated to their associated common terms.

In certain embodiments, there is also a feature providing notifications to users (Healith™ notifications).

Embodiments of the present disclosure further relate to methods of monitoring the quality of data input into the centralized repository, as maintaining the quality of the input of searchable data/profiles is critical. To detect erroneous and/or potentially erroneous code selections during profile submissions, code selected from multiple chapters via one submission may be flagged as potentially incorrect, which, if in correctly, may lead to incorrect search results. For example, in many embodiments, a pop-up message may appear when submitting pursuant to the first step of the profile submission process (code selection) asking them to reconsider and go back, or continue. As the amount of data stored in the system increases the ability to detect patterns within groups of codes submitted together may improve as well, including the ability to make suggestions to members. For example, based on previously submitted groups of selected Healith™ classification system codes, the system may prompt a member to determine whether an omitted Healith™ classification system codes should have been included with the group of Healith™ classification system codes.

Embodiments of the present disclosure further describe inputting healthcare information of healthcare participants (e.g., members). The healthcare information may be organized and stored for retrieval in response to a search. In general, members submit information via a three-step process that involves selecting one or more classification system codes and/or one or more profiles, and completing a profile specific questionnaire. This information relates to a unique member profile that may be retrieved in response to a search. Members may submit unlimited submissions for any profile. In this way, the invention of the present disclosure provides a global search system for healthcare information.

The first step relates to selecting classification system codes relevant to a submission. The second step relates to tying the selected classification codes to a specific type of healthcare participant via selection of one or more profiles. Profiles include, but are not limited to, consumer, providers, policy & regulatory, services & solutions, products & devices, advocacy and philanthropy, employment, research and education. In general, the profiles provide another layer of specificity when searching for healthcare participants and information. The profiles provide a framework within which the invention of the present disclosure provides opportunities for different users to self-select their focus in healthcare and communicate (e.g., consumers to providers, providers to consumers, researchers to consultants, app developers to investors, consumers to consumers, advocates to insurance companies, policymakers to providers, etc.). The third step relates to completing profile specific questionnaire forms. These questionnaires include requests for general information (e.g., information requested in each questionnaire, regardless of the profile) as well as requests for information unique to particular profiles. All submitted information is searchable by one or more of the classification codes selected in the first step, profile selected in the second step, and selected key terms selected in the third step. For a member's information to result in a user search there must be an exact match of the code, profile, and at least one keyword. Amount of matched criteria will be considered by the algorithm when ranking search results.

FIG. 1 is a flowchart of a method of providing healthcare information, according to an embodiment of the present disclosure. In general, programming languages may include PHP, HTML, CSS, and/or JavaScript. Data may be stored via MySQL. The base platform may include SocialEngine PHP. The framework and library technologies may include Send Framework (PHP), Mootools (JS), and/or jQuery (JS). Blockchain technology may also be utilized by this system.

At step 101, healthcare information for a plurality of members is stored in a database (e.g., SQL database). Healthcare information may include information relating to one or more of diseases, symptoms, abnormal findings, complaints, social circumstances, external causes of injuries and/or diseases, as well as information relating to one or more of various products, services, procedures (e.g., based on CPT codes in profile questionnaires) and programs provided by one or more of the plurality of members. The healthcare information to be stored may include information submitted by each of the plurality of members in response to questionnaires. In general, the questionnaires include information specific and/or unique to each profile (e.g., consumers, providers, insurers, policy and regulatory, products and devices, services and solutions, advocacy and philanthropy, research, education, and employment) and/or information specific to classification system codes. Each member may create multiple profiles and they also may submit multiple questionnaires for each profile. In many embodiments, a member may complete multiple questionnaires for a single profile. For example, a single profile may include a separate questionnaire for each code in which the member offers a program and/or service. The information submitted via questionnaires may be edited at any time by the member. In addition to being the information stored, the information included in members' responses may include the information presented to a user in response to a search.

In many embodiments, the questionnaire is a form with fields for entering information specific to the user-selected profile and classification system codes. Different forms may be created for specific profiles and then called via a controller file based on a user-selection. For example, a parameter type may be retrieved from the controller file and then utilized to call the form function:

---

$this->view->type = $type = $this->_getParam('type', 0); //getting the type of selected profile here.

---

In some embodiments, routines may be utilized to check whether a type is set to 0 to redirect the user to the first page again in instances where the user may be seeking access to a page without visiting the first page and/or without utilizing special identification parameters. The form function called may depend on the user-selected profile:
$formClass='Healthlinea_Form_Profiles_'.
$profileApi>getTypeForm($type).

A dynamically generated form may be retrieved and sent to view:
$this->view->form=$form=new $formClass( ).

The view file may include code for generating the view/layout and include html, css, and/or javascript code for form validation. Once the user "submits," the code validates data present in the required fields. In many embodiments, the form is validated before the information is stored in the database. Parameters may be arranged in table columns so each value does not need to be saved one by one. The array may be passed as an argument and stored obviating the need to repeatedly link the database over and over again.

Healthcare information submitted by each of the plurality of members may be stored in a database. Two tables may be utilized for storing the fields and input data (e.g., healthcare information) corresponding to specific fields in the database. A first table may be defined as engine4_healthlinea_profiles for storing the input data. For example, the first table may include initial data relating to the classification system selected by the user during the first step of the creation of a profile and the type of profile (e.g., consumer, provider, etc.) A second table may be defined as engine4_healthlinea_fields for storing the fields corresponding to requested input data. For example, the second table may include fields for a consumer profile, such as, screenname, website, experience with selected classification system code, a description of the healthcare information, among other things. The first table and the second table may include a 1:1 relation, with the first table as the parent table.

The table may be called and prepared to store the input data from the form via the following:

```
$profileTabel = Engine_Api::_( )->getDbTable('profiles', 'healthlinea');
$fieldsTabel = Engine_Api::_( )->getDbTable('fields', 'healthlinea');
```

Data may be stored/saved to the database via the following:

```
$profile = $profileTabel->createRow( );
$profile->setFromArray(array(
   'owner_id' => (loggedin in user id),
   'icd_id' => (selected ICD id),
   'profile_type' => (Type of selected profile)
   'creation_date' => (current date)
));
$profile->save( );
```

Any photographs and/or images may be stored via the following:
$profile->setPhoto(Photo Param goes here);
Now store the profile questing data.

```
$profileData = $fieldsTabel->createRow( );
$profileData->setFromArray(array of inputs);
$profileData->save( );
```

Upon storing/saving the data to the database, the user may be redirected to a page listing each profile completed by the user/member.

A user/member may edit a form. To edit a form, the code may include extra parameters to determine whether the user is a creator of the profile, among other things, to protect information from improper modifications and/or alterations to the data. A special profile identification number may be assigned by the database and retrieved via the following:
$profile_id=$this->_getParam('id', 0);

The profile retrieved may be limited to the profile of the current user and retrieved via the following:

```
$viewer_id = Engine_Api::_( )->user( )->getViewer( )->getIdentity( );
$profileTabel = Engine_Api::_( )->getDbTable('profiles', 'healthlinea');
$select = $profileTabel->select( )
    ->where('profile_id = ?', $profile_id)
    ->where('owner_id = ?', $viewer_id)
;
$profile = $profileTabel->fetchRow($select);
```

If no such profile exists, a user may be presented with a private page error via the following:

```
if(!$profile) {
    return $this->_forward('requireauth', 'error', 'core');
}
```

If a profile exists, the type of profile may be sent to view file, with some front end validations included, via the following:
$this->view->type=$profile->profile_type;

The file is an API file that includes all of the fields included in the questionnaires. In some embodiments, the fields may not be stored in the database to minimize the number of connections to the database:
$profileApi=Engine_Api::_( )->getApi('profiles', 'healthlinea');

To generate the form and send the form to view file (which is responsible for layouts), the following may be used:

```
$formClass = 'Healthlinea_Form_Profiles_' .
$profileApi->getTypeForm($profile->profile_type);
$this->view->form = $form = new $formClass( );
```

The label for the submit button may be changed to "Submit & Edit another Submission" via the following:
$form->sub_mit->setLabel('Submit & Edit another Submission');

The responses to the fields in a questionnaire may be retrieved in order to re-populate the form with the submitted information:

```
$fieldsTabel = Engine_Api::_( )->getDbTable('fields', 'healthlinea');
$selectFields = $fieldsTabel->select( )
    ->where('profile_id = ?', $profile_id)
;
$profileFields = $fieldsTabel->fetchRow($selectFields);
```

In some embodiments, looping routines may be utilized to check if the selected profile includes the data in the special array format via the following:

```
$prePopArray = array( );
foreach ($profileFields->toArray( ) as $key => $value) {
    $checkBoxes = array(
        'programs_and_services',
        'physician_specialty',
```

-continued

```
    'provider_type',
    'population_served',
    'service_type',
    'org_focus',
    'provider_types',
    'product_type',
    'service_solution_focus',
    'area_of_focus',
    'type_of_advocacy',
    'org_type',
    'degree_type',
    'degree_program',
    'institute_accreditation',
    'emp_position',
    'salary_range',
    'package_options',
    'plan_options',
    'specialty_type',
    'facility_type',
    'plan_type',
    'accreditations',
    'topics_and_issues',
    'organization_types',
    'organization_jurisdiction',
    'focus',
    'student_degree_type',
    'student_degree_program',
    'educator_degree_type',
    'educator_degree_program',
    'educator_accreditation',
    'salary_range'
    );
    if( in_array($key,$checkBoxes) ){
        $value = explode(',', $value);
    }
    $prePopArray[$key] = $value;
}
```

The form may be pre-populated via the following:
$form->populate($prePopArray);

A user may then change the fields and hit edit button to update the database records.

At step 102, one or more classification system codes (e.g., Healith™ classification system codes, ICF, etc.) and one or more profiles may be associated with the stored healthcare information. The one or more profiles may include one or more of consumers, providers, insurers, policy and regulatory, products and devices, services and solutions, advocacy and philanthropy, research, education, and employment. Unlimited submissions of codes associated with profiles may be submitted by members.

At step 103, the stored healthcare information is retrieved from the database in response to a classification system code signal. The information may be organized within each profile. In many embodiments, the Healith™ classification system code signal may be generated in response to a user-defined input (e.g., parameters submitted by user via a search form). A user-defined input may include one or more of codes, profiles, keywords, and area codes.

A search query may include parameters submitted by the user (e.g., the user-defined input) and linking a first table and a second table. In some embodiments, linking the first table and the second table may include reducing the database call. In some embodiments, the tables may be initialized for use in searching. For example, the following may be utilized to initialize the tables:

```
$profileTable = Engine_Api::_( )->getDbTable('profiles,' 'healthlinea');
$profileTableName = $porfileTable->info('name');
$fieldsTable = EngineApi::_( )->getDbTable('fields', 'healthlinea');
$fieldsTableName = $fieldsTable->info('name').
```

In some embodiments, a search query may be created to retrieve records. For example, the search query may include the following:

```
$select = $profileTabel->select( );
$select->setIntegrityCheck(false)->from($profileTableName, array('*'));
$select->join($fieldsTabelName,"'{$fieldsTabelName}'.'profile_id'='{$profileTableName}'.profile_id", array('*'));
$select->where("$profileTableName.icd_id = $icd");
$select->where("$profileTableName.profile_type = $type").
```

In some embodiments, a user may resubmit a zip code to conduct a search in a zip-code column of the database:

```
if(!empty($params['zip_code'])){
    $zip = $params['zip_code'];
    $select->where("$fieldsTabelName.zip_code LIKE '%$zip%' ");
}.
```

In some embodiments, upon completing a search query, the following instructs the database to run the query and present results:

$paginator=Zend_Paginator::factory($select).

In some embodiments, the following may instruct the database to return a specified number of search results (e.g., 5):

$paginator->setItemCountPerPage(5).

In some embodiments, the follow may instruct the database to return search results from a specific page:

$page=$this->_getParam('page', 1); $paginator->setCurrentPageNumber($page).

In some embodiments, the following may instruct the database to send the results to view files:

$this->view->paginator=$paginator.

The following further illustrates the present invention:

```php
<?php public function createAction() {

//get the type of selected profile on profile selection step $this->view->type = $type = $this->_getParam('type', 0);
```

```
/*
 * get the session data we stored on the ICD selection step, we cannot pass along as a parameter because
 * this data can be big and URL limit can be issue
 */

$session_icdtype = new Zend_Session_Namespace('Healthlinea_Profile');

$preDate = $session_icdtype->icd_type;

/* Check if the user is trying to access the URL without following the first step,
 * set a flag to true in order to redirect in next condition */

$start = false;

if (empty($preDate)) {

$start = true;

} elseif (!isset($preDate['icd_list']) || empty($preDate['icd_list'])) {

$start = true;

} elseif (!isset($preDate['type']) || empty($preDate['type'])) {

$start = true;

} elseif (!$type) {

$start = true;

}

/* start over to first page incase user is trying to
 * access the page directly without first page
```

```
*/
if ($start) { return $this->_helper->redirector->gotoRoute( array(

'module' => 'healthlinea',

'controller' => 'profile',

'action' => 'type'

), 'default', true

);

}
/* Prepare the tables for creating profiles */

$profileApi = Engine_Api::_()->getApi('profiles', 'healthlinea');

//Pass the ICD selected list data to view in order to show the list of selected options $this->view->icd = $preDate['icd_list'];

//get the selected profile type human readable name $this->view->profile = $profileApi->getProfileTypes($type);

//get form object $formClass = 'Healthlinea_Form_Profiles_' . $profileApi->getTypeForm($type);

//pass the form to view $this->view->form = $form = new $formClass();

//check if user is trying to submit or not
```

```
if (!$this->getRequest()->isPost()) { return;

}

//FORM VALIDATION, User is trying to submit the data, check if the data is valid if (!$form->isValid($this->getRequest()->getPost())) { return;

}

//get user's submitted data $values = $form->getValues();

/* for some special profiles, need to check required fields conditionally,

* This is just in case user tries to do something in browser and can bypass the browser validation

* but this validation will occur in that case

*/ if ($type == 9) { if ($values['edu_you_type'] == 'educator') {

$form->educator_institute_name->setRequired(true);

$form->educator_country->setRequired(true);

$form->educator_street_adrs->setRequired(true);

$form->educator_state->setRequired(true);

$form->educator_city->setRequired(true);
```

```php
    $form->educator_zip_code->setRequired(true);

$form->educator_description->setRequired(true);

$form->educator_website->setRequired(true);

$form->educator_degree_type->setRequired(true);

$form->educator_degree_program->setRequired(true);

$form->educator_email->setRequired(true);

$form->educator_phone->setRequired(true);

$form->educator_first_name->setRequired(true);

$form->educator_last_name->setRequired(true);

$form->educator_position->setRequired(true);

$form->educator_accreditation->setRequired(true);

$form->educator_distance_learning->setRequired(true);

} if ($values['edu_you_type'] == 'student') {

$form->student_first_name->setRequired(true);

$form->student_last_name->setRequired(true);

$form->student_degree_type->setRequired(true);

$form->student_degree_program->setRequired(true);

}

//FORM VALIDATION, maybe above requirements are not met correctly if (!$form->isValid($this->getRequest()->getPost())) {
```

```
        return;

}

}

/* for some special profiles, need to check required fields conditionally,

* This is just in case user tries to do something in browser and can bypass the browser validation

* but this validation will occur in that case

*/ if ($type == 10) { if ($values['empl_you_type'] == 'Job Seeker') {

$form->job_position->setRequired(true);

$form->job_zip_code->setRequired(true);

$form->job_first_name->setRequired(true);

$form->job_last_name->setRequired(true);

$form->resume->setRequired(true);

$form->date_available->setRequired(true);

} if ($values['empl_you_type'] == 'Employer') {

$form->org_name->setRequired(true);

$form->org_mission->setRequired(true);

$form->website->setRequired(true);

$form->emp_position->setRequired(true);
```

```
$form->employer_job_desc->setRequired(true);

$form->country->setRequired(true);

$form->street_adrs->setRequired(true);

$form->state->setRequired(true);

$form->zip_code->setRequired(true);

$subForm = $form->getSubForm('salary_range');

$subForm->min->setRequired(true);

$subForm->max->setRequired(true);

$form->email->setRequired(true);

$form->phone->setRequired(true);

$form->position_title->setRequired(true);

$form->first_name->setRequired(true);

$form->last_name->setRequired(true);

}

//FORM VALIDATION, maybe above requirements are not met correctly if (!$form->isValid($this->getRequest()->getPost())) { return;

}

}

/* Ready to insert the data into system

* Initialize the db tables to start inserting process
```

*/

/* Table engine4_healthlinea_profiles,

* this is the main table for storing the initial data for profile type

* This holds the basic data and chapter id, profile type creation date etc

*/

$profileTabel = Engine_Api::_()->getDbTable('profiles', 'healthlinea');

/* Table engine4_healthlinea_fields

* This table holds the questionaries data

*/

$fieldsTabel = Engine_Api::_()->getDbTable('fields', 'healthlinea');

/* Table engine4_healthlinea_masters

* This table just holds a master id of profiles, in case if user trying to add the extra chapters

* to same profiles created before, it helps to control the logic, much used much only holds one important id

*/

$masterTable = Engine_Api::_()->getDbTable('masters', 'healthlinea');

/* Table engine4_healthlinea_profileprocedures

* This tables holds the data of selected procedures

*/

$profileprocedureTable = Engine_Api::_()->getDbTable('profileprocedures', 'healthlinea');
// create a master id first

```
$master = $masterTable->createRow();

$master->setFromArray(array(

'user_id' => Engine_Api::_()->user()->getViewer()->getIdentity()

));

$master->save();

//each profile for each icd $photo_id = 0;

$profile_ids = array();

$fieldValues = '';

//itreate the ICDS to create profiles foreach ($preDate['icd_list'] as $icd_id) {

$profile = $profileTabel->createRow();

$profile->setFromArray(array(

'owner_id' => Engine_Api::_()->user()->getViewer()->getIdentity(),

'icd_id' => $icd_id,

'profile_type' => $preDate['type'],

'creation_date' => new Zend_Db_Expr('NOW()'),

'master_id' => $master->master_id

));
```

```
$profile->save();

//if user has uploaded any photo in case if (!empty($_FILES['photo']) && $photo_id == 0) {

//no errors if ($_FILES['photo']['error'] == 0) {

$profile->setPhoto(APPLICATION_PATH . '/public/temporary/' . $values['photo']);

$photo_id = $profile->photo_id;

}
} if ($photo_id != 0) {

$profile->photo_id = $photo_id;

$profile->save();

}

$profile_ids[] = $profile->profile_id;

//store the procedures $procedures = $_POST['procedures'];

if (isset($procedures) && !empty($procedures)) {

$pro = array_values($procedures);

$json_profile_procedure = json_encode($pro);

$procedure = $profileprocedureTable->createRow();

$procedure->setFromArray(array(
```

```
    'owner_id' => Engine_Api::_()->user()->getViewer()->getIdentity(),

'profile_id' => $profile->profile_id,

'procedure_id' => $json_profile_procedure,

'creation_date' => new Zend_Db_Expr('NOW()')

));

$procedure->save();

}

//add fields data $fields = array_merge($values, array('profile_id' => $profile->profile_id));

$filteredFields = array();

//manage array values to store in database.

foreach ($fields as $key => $value) { if (is_array($value)) {

$value = implode(',', $value);

}

$filteredFields[$key] = $value;

}

$fieldValues = $filteredFields;

$profileData = $fieldsTabel->createRow();

$profileData->setFromArray($filteredFields);

$profileData->save();
```

```
}

//go to end, after creating the profile, redirect user to list of created profiles, with master id
return $this->_helper->redirector->gotoRoute(
    array(
        'module' => 'healthlinea',
        'controller' => 'profile',
        'action' => 'created',
        'type' => $this->view->type,
        'master_id' => $master->master_id
    ), 'default', true
);
}
```

The following Examples are intended to illustrate the above invention and should not be construed as to narrow its scope. One skilled in the art will readily recognize that the Examiners suggest many other ways in which the invention could be practiced. It should be understood that numerous variations and modifications may be made while remaining within the scope of the invention.

Example 1

Creating a Healith™ Account

Individuals and organizations may create a master account. They can have multiple profiles under their master account. Profile-specific questionnaires have been created for each profile. Multiple questionnaires may be submitted for each profile. These questionnaires focus on gathering certain information tied to the chosen classification system codes and presented as a result of a search.

After creating a master account, the first step to completing a profile questionnaire is selecting the codes which will be listed by expandable chapter. Due to the way in which the databases are structured it is important to be specific and take it one health category at a time, or even one specific code at a time. Creating a profile should take several rounds of questionnaire submissions for most organizations.

For example, a healthcare system may consist of hospitals and outpatient services. They may also have an insurance arm and investments in private sector technology which include apps developed to help manage chronic conditions. The healthcare system created a master account and is starting to complete a provider profile. As a provider, the healthcare system offers a multitude of healthcare services. Each service may be treated independently when creating (or editing) their provider profile. For example, the healthcare system should not select the codes related to their primary care services and cardiac surgery services in the same questionnaire submission. Instead, they should select the codes related to one program or service (ex, heart disease), complete the questionnaire form with responses related to their heart disease program, submit, and then go through the same steps for another program or service.

Once the user submits the questionnaire form, the responses may be tied to the codes they selected in the first step. When a user conducts a search for any of those codes and selects the provider profile, the information the healthcare system submitted in the questionnaire will result. Each questionnaire may include a field flagged as the keyword search field. The options within that field may be presented to the user during the keyword search step, providing a second layer of search specificity in addition to the selected. The healthcare system may follow the same steps and complete their insurance & payors profile to promote their insurance products. They may also encourage the app developer to create an account and complete their services & solutions profile to promote the apps.

This unique platform allows users anywhere in the world to find the information they want. Additionally, in the questionnaire, members may provide their contact information, allowing users to contact them directly through their preferred method of contact. Members may also send and receive messages through the system.

Members may edit and maintain their profiles. Allowing and assisting members to input their information and maintain their profiles helps ensure accuracy. It is in the best interest of the member to ensure their information is accurately resulting in a user search.

Additional features such as blogs, instant chat, likes, events, calendars, polls and matches are available to members at their selection.

To create Healith classification systems for diagnosis, diseases, conditions and environmental factors, WHO classification systems were not found online in a readily available format to be utilized in the way required by this website. Each chapter and all of its contents were downloaded into a spreadsheet format and then manually manipulated into the required format suitable for the present purposes. Many subchapters had subcategories that were not assigned a numeric code by the WHO. In order for these subcategories to be searchable in the centralized repository database, the subcategories had to be given a numeric code through creating a formula in a spreadsheet that added a decimal at the end of the number code of the parent, and increased by one-one hundredth until the next parent that had a numeric code. These codes are proprietary, not used elsewhere and should not be considered part of the WHO classification system. Their purpose is for allowing the subcategories to be selected individually for users and members.

Example from WHO

E00.0 Congenital iodine-deficiency syndrome, neurological type
    Endemic cretinism, neurological type
E00.1 Congenital iodine-deficiency syndrome, myxedematous type
    Endemic hypothyroid cretinism
    Endemic cretinism, myxedematous type Example of Manipulated Chapters E00.0 Congenital iodine-deficiency syndrome, neurological type
E00.0.01 Endemic cretinism, neurological type
E00.1 Congenital iodine-deficiency syndrome, myxedematous type
E00.1.01 Endemic hypothyroid cretinism
E00.1.02 Endemic cretinism, myxedematous type Then common terms were concatenated, manually in excel, to the ICD. The standard nomenclature for Healith classification system is (common term) formal medical term. There can be multiple common terms separated by a comma for each formal medical term, and the same common terms for individual formal terms.

Example of Healith Classification System for Diagnosis, Diseases, Conditions, Environmental Factors

| |
|---|
| (Lumpy jaw) Actinomycosis |
| (Lumpy jaw) Pulmonary actinomycosis |
| (Lumpy jaw) Abdominal actinomycosis |
| (Lumpy jaw) Cervicofacial actinomycosis |
| (Lumpy jaw) Actinomycotic sepsis |
| (Lumpy jaw) Other forms of actinomycosis |
| (Lumpy jaw) Actinomycotic meningitis |
| (Lumpy jaw) Actinomycotic encephalitis |
| (Lumpy jaw) Actinomycosis, unspecified |

In Healith when members submit their profile questionnaires and assign Healith classification system codes to the information, they are given the option to add common terms to any Healith Code. Once approved by Healith admin the common term would be available throughout Healith for all users and members. This type of crowd sourcing ensures that common terms transcend geographic and language barriers. More importantly it allows anyone to search for information and connect with others with the all the specificity allowed by current medical terminology.

Health classification system codes is the name for several categories of this type of association of common term with formal term. Currently there are Health classification systems for diagnosis, diseases, conditions and environmental factors based on ICDs. There will also be Health classification system codes for procedures, based on the Current Procedural Terminology classification system, and other nationally recognized system.

Figure 2:
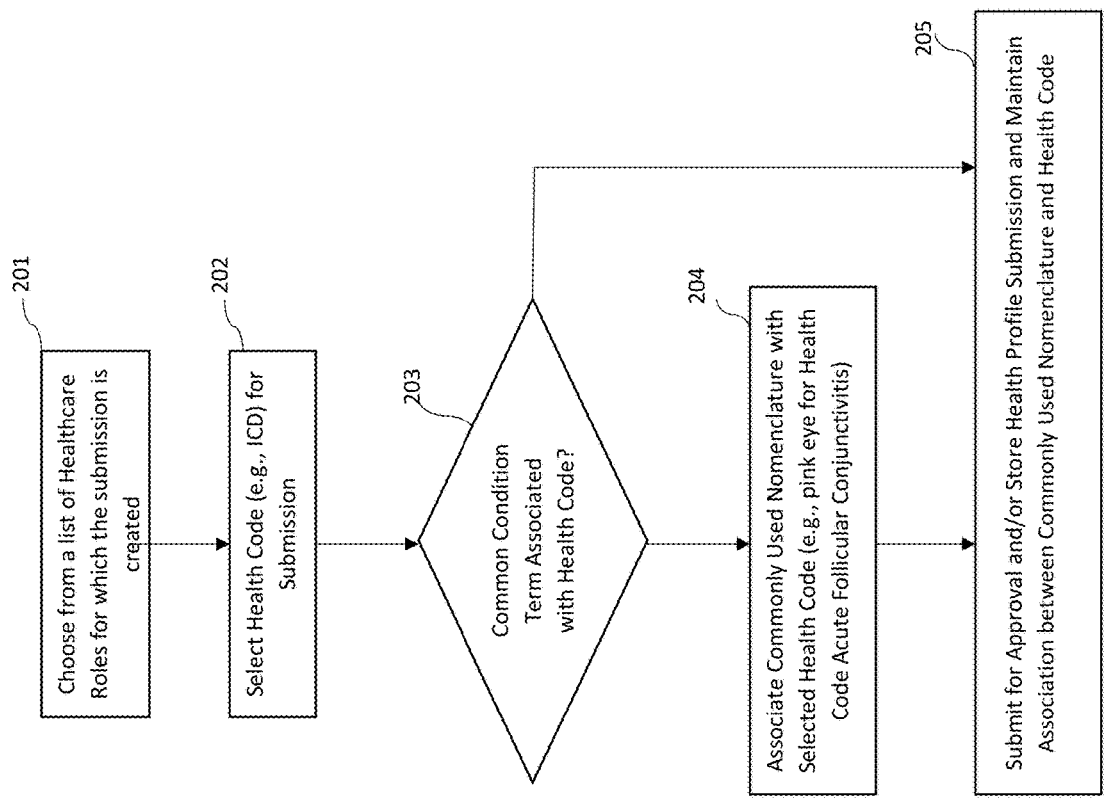
FIG. 2 is a flowchart illustrating a process for creating submissions, which may include information regarding a disease, services providers, treatments available, etc. according to one embodiment.

FIG. 2 is a flowchart illustrating a process for creating submissions, which may include information regarding a disease, services provides, treatments available, etc. For example, a physician may specialize in a particular field (e.g., ophthalmology), and may create one or more submissions related to various conditions/diseases that the physician treats (e.g., glaucoma, detached retina, etc.). The physician may create one submission directed to glaucoma, which may include glaucoma diagnosis and/or treatment. The physician may create another submission directed to detached retina, including symptoms and/or treatment. The submission is stored in a centralized location, and is searchable by keywords. In addition, as discussed in more detail below, while particular conditions/diseases may be identified by a scientific name or medical code (e.g., using one or more World Health Organization (WHO) classification systems codes), commonly used condition terms may be associated with the medical codes to allow users to search using commonly used condition terms. In one embodiment, crowd-sourcing techniques may be utilized to associate commonly used condition terms with the scientific names or health codes, even if the particular entity creating a submission is not aware of the commonly used condition term. For example, a physician may create a submission that indicates that the physician is adept at treating acute follicular conjunctivitis. Separate submissions by other entities (healthcare consumers; physicians) may indicate that acute follicular conjunctivitis is commonly known as "pink eye". Subsequently, a healthcare consumer (e.g., patient) conducting a search for pink eye symptoms may be directed to the submission provided by the physician, despite the fact that the physician was not initially responsible for making the association between the term acute follicular conjunctivitis and the commonly known term pink eye. In this way, some embodiments of the present invention provide a way of bridging the gap between scientific names/health codes and the terms used by non-physicians to describe conditions/diseases.

At step 201 a user and/or entity creating the submission selects a healthcare role that describes the entity. In one embodiment, healthcare roles include one or more of: 1.) Healthcare Consumer; 2.) Health and Medical Information Provider; 3.) Physician or Provider; 4.) Payor; 5.) Policy or Regulatory Organization; 6.) Product, Device, or Pharmaceutical Developer; 7.) Other Services Provider; 8.) Advocate or Philanthropist; 9.) Researcher or Grantor; 10.) Educator or Student; and/or 11.) Employer or Job Seeker. Subsequent searches by users can be directed to submissions provided by select healthcare profiles. For example, a patient looking for physicians may limit a search to submissions provided by physicians and/or providers.

At step 202, the user and/or entity creating the health profile submission selects a health code that identifies the condition/disease for which the submission is being created. For example, in some embodiments, the WHO classification system codes are utilized. Examples of WHO classification system codes includes the International Classification Disease (ICD) codes.

At step 203, the user and/or entity creating the submission is prompted to determine whether a common condition term can be associated with the health code selected at step 202. For example, as discussed above, the health code acute follicular conjunctivitis may be selected. At step 203, the user and/or entity is prompted for common condition terms. In some instances, the user and/or entity may be aware that acute follicular conjunctivitis may also be known as "pink eye".

At step 204, if the user/entity is aware of a common condition term that can be associated with the health code selected at step 202, then the user provides the common condition term. For example, having selected the health code associated with acute follicular conjunctivitis at step 202, the user/entity would associate the term "pinkeye" with this health code at step 204. If the user/entity is not aware of a common condition term for the selected health code, then no common condition term is associated with the health code.

At step 205, the submission is submitted for review and/or stored as part of the central repository to allow users to subsequently search the submission. If approved, the submission is made available to others. In addition, if approved, the common condition term provided at step 204 is associated with the health code so that subsequent searches utilizing the common condition term will direct users to submissions associated with the associated health code, including those submissions that did not originally include the common condition term. In this way, embodiments of the present invention allow for the crowdsourcing of common condition terms that should be associated with health codes. A benefit of this approach is that it allows users from a plurality of different language backgrounds to search and communicate without knowledge of scientific/medical names. For example, the common condition term for acute follicular conjunctivitis in one region may be "pinkeye', while the common condition term for the same condition in another region may differ. A submission that associates the common condition term with the associated health code (i.e., scientific or medical term) creates an associate that allows users to search for submissions related to the health code based only on the common condition term.

Figure 3:
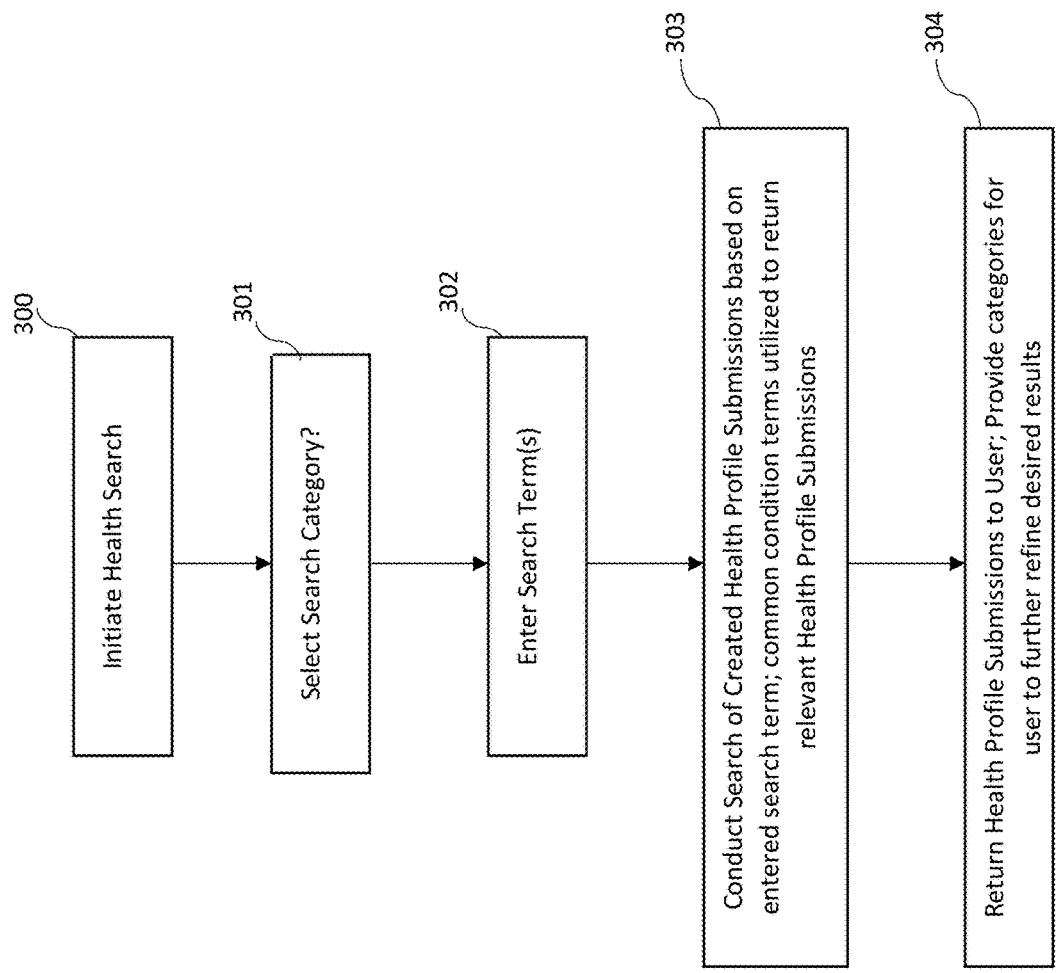
FIG. 3 is a flowchart illustrating a process for searching submissions previously created and approved according to one embodiment.

FIG. 3 is a flowchart illustrating a process for searching submissions previously created and approved. At step 300, a health search is initiated by a user/entity. At step 301, a search category may be selected. In some embodiments, a user may simply conduct a search on all categories, but in other embodiments may wish to select a particular sub-set or category to search. In some embodiments, categories may include one or more of: 1.) Diseases, Diagnosis, Condition (based on health codes); 2.) Common Condition Terms (searches terms that are associated with health codes); 3.) Environmental Factors; 4.) Symptoms; and 5.) Treatments. Having selected a search category at step 301, at step 302 a search box is provided that allows the user/entity to enter the search terms. If the user does not select a search category at step 301, the user may instead simply enter the search terms directly into a search box, with the result being that all search categories are searched. In some embodiments, users identified as patients or healthcare consumers would not be provided with the option of searching based on health codes, but rather would be prompted to search based on common condition terms.

At step 303, a search is conducted on the search terms provided. In response to a user/entity providing health codes (e.g., ICDs), then submission are returned based on matching health codes. This operation is akin to typical searches, in which a keyword search is conducted based on the keyword entered. However, if search terms provided by the user correspond with common condition terms (either based on the search category selected or based on the identification of the user), then a search is conducted using the common condition term. The search identifies the health codes associated with the common condition term provided, and returns submissions associated with the identified health codes.

At step 304, submissions are returned to user along with categories associated with the submissions that allow the user to select to further refine desired results. In one embodiment, the categories are those selected by the user/entity when creating the submissions. For example, as described with respect to FIG. 2, the categories may include one or more of: 1.) Healthcare Consumer; 2.) Health and Medical Information Provider; 3.) Physician or Provider; 4.) Payor; 5.) Policy or Regulatory Organization; 6.) Product, Device, or Pharmaceutical Developer; 7.) Other Services Provider; 8.) Advocate or Philanthropist; 9.) Researcher or Grantor; 10.) Educator or Student; and/or 11.) Employer or Job Seeker.

For example, a patient looking for a doctor to treat "pinkeye" may at step 301 select the category Common Condition Terms (searches terms that are associated with health codes) to initiate the search (for example, if the patient does not know the health code associated with "pinkeye"). At step 302, the patient/user then enters the term "pinkeye" into the search box, and a search is conducted for the term "pinkeye". At step 303, assuming the term "pinkeye" that has been previously associated with the health code acute follicular conjunctivitis, then the search returns results (e.g., submissions) associated with the health code acute follicular conjunctivitis. At step 304, the results are returned to the user, and the user is given the option of further refining the results based on one or more categories. For example, in this example the patient/user is looking for a physician to treat the condition, so the patient/user may filter by the category Physician or Provider. The filtered results would therefore include submissions provided by physicians and/or providers that provide treatment for "pinkeye" or acute follicular conjunctivitis.

Figure 4:
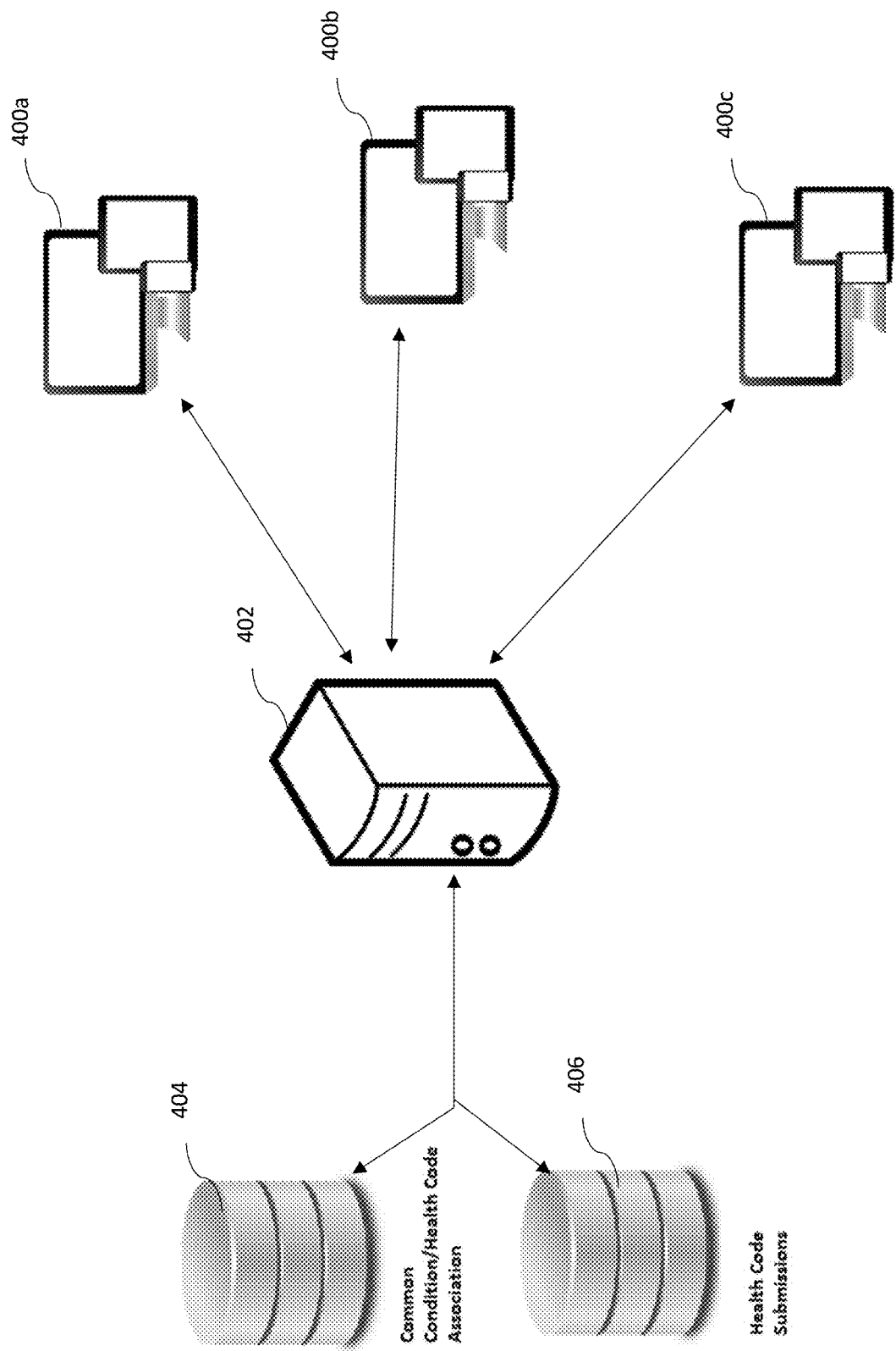
FIG. 4 is a block diagram that illustrates a system of collecting, associating, storing, searching, providing, and creating healthcare information according to one embodiment.

FIG. 4 is a block diagram that illustrates a system of collecting, associating, storing, searching, providing, and creating healthcare information according to an embodiment of the present invention. The embodiment shown in FIG. 4 includes a plurality of users or participants 400a, 400b, 400c, a healthcare server 402, common condition/health code association database 404 and health code submission database 406. Participants 400a, 400b, and 400c may access the system via any internet enabled device, including computers, tablets, and cellphones. Participants interact with healthcare server 402, which interacts with participants to collect submissions as described with respect to FIG. 2 and to receive search queries and to return results as described with respect to FIG. 3. Received submissions (for example, those created by physicians) are stored to health code submissions database 406. As discussed above, these submissions are searchable by, among other things, health codes (e.g., ICD codes). As discussed above, in addition to health codes, the system described in FIG. 4 also allows users to use common condition terms to search, and crowdsources the ICD codes that should be associated with common condition terms. The associations between one or more common condition terms and an ICD code is stored in common condition/health code association database 404. In some embodiments, common condition/health code association database 404 and health code submission database 406 are implemented on a single piece of hardware, with logical associations implemented in separate tables. A benefit of this association, is that users accessing the system are able to contribute associations between common condition terms (e.g., pinkeye) and health codes (e.g., acute follicular conjunctivitis). A subsequent search submitted by a participant (e.g., participant 400a) on the term "pinkeye" is received by healthcare server 402. A query is provided by healthcare server 402 to common condition/health code association database 404 with the common condition term (e.g., "pinkeye"), and returns in response the associated health code (e.g., acute follicular conjunctivitis). The received health code is then utilized to query the health code submissions database 406 in order to retrieve submissions associated with the received health code. In this way, users without knowledge of scientific, medical health codes are allowed to interact with the system to retrieve relevant information. In addition, participants with experience in WHO classification system codes are able to create a framework to organize information, while making it accessible to participants unfamiliar with the WHO classification system.

Other embodiments of the present disclosure are possible. Although the description above contains much specificity, these should not be construed as limiting the scope of the disclosure, but as merely providing illustrations of some of the presently preferred embodiments of this disclosure. It is also contemplated that various combinations or sub-combinations of the specific features and aspects of the embodiments may be made and still fall within the scope of this disclosure. It should be understood that various features and aspects of the disclosed embodiments can be combined with or substituted for one another in order to form various embodiments. Thus, it is intended that the scope of at least some of the present disclosure should not be limited by the particular disclosed embodiments described above.

Thus, the scope of this disclosure should be determined by the appended claims and their legal equivalents. Therefore, it will be appreciated that the scope of the present disclosure fully encompasses other embodiments which may become obvious to those skilled in the art, and that the scope of the present disclosure is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present disclosure, for it to be encompassed by the present claims. Furthermore, no element, component, or method step in the present disclosure is intended to be dedicated to the public regardless of whether the element, component, or method step is explicitly recited in the claims.

The foregoing description of various preferred embodiments of the disclosure have been presented for purposes of illustration and description. It is not intended to be exhaustive or to limit the disclosure to the precise embodiments, and obviously many modifications and variations are possible in light of the above teaching. The example embodiments, as described above, were chosen and described in order to best explain the principles of the disclosure and its practical application to thereby enable others skilled in the art to best utilize the disclosure in various embodiments and with various modifications as are suited to the particular use contemplated. It is intended that the scope of the disclosure be defined by the claims appended hereto Computer System & Architecture The invention can be implemented in digital electronic circuitry, or in computer hardware, firmware, software, or in combinations of them. Apparatus of the invention can be implemented in a computer program product tangibly embodied in a machine-readable storage device for execution by a programmable processor; and method steps in the invention can be performed by a programmable processor execution a program of instructions to perform functions of the invention by operating on input data and generating output. The invention can be implemented advantageously in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object-oriented programming language, or in 50 assembly or machine language if desired; and in any case, the language can be a compiled or interpreted language.

Suitable processors include, by way of example, both general and special purpose microprocessors. Generally, a processor will receive instructions and data from a read-only memory and/or a random-access memory. Generally, a computer will include one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and optical disks. Any of the foregoing can be supplemented by, or incorporated in, ASICs (application-specific integrated circuits).

Figure 5:
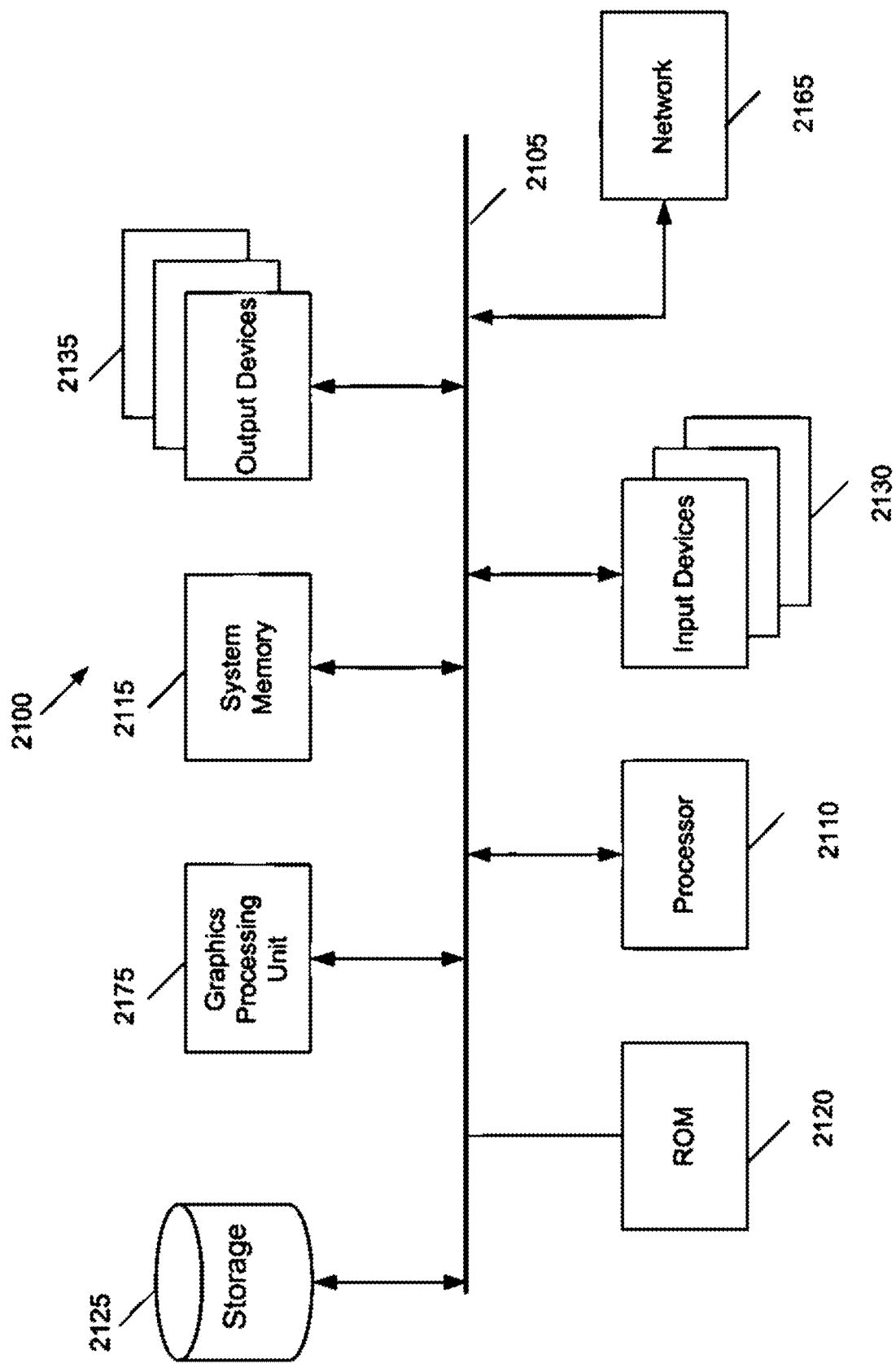
FIG. 5 is a block diagram that illustrates the hardware of the system of one embodiment of the invention.
Figure 6:
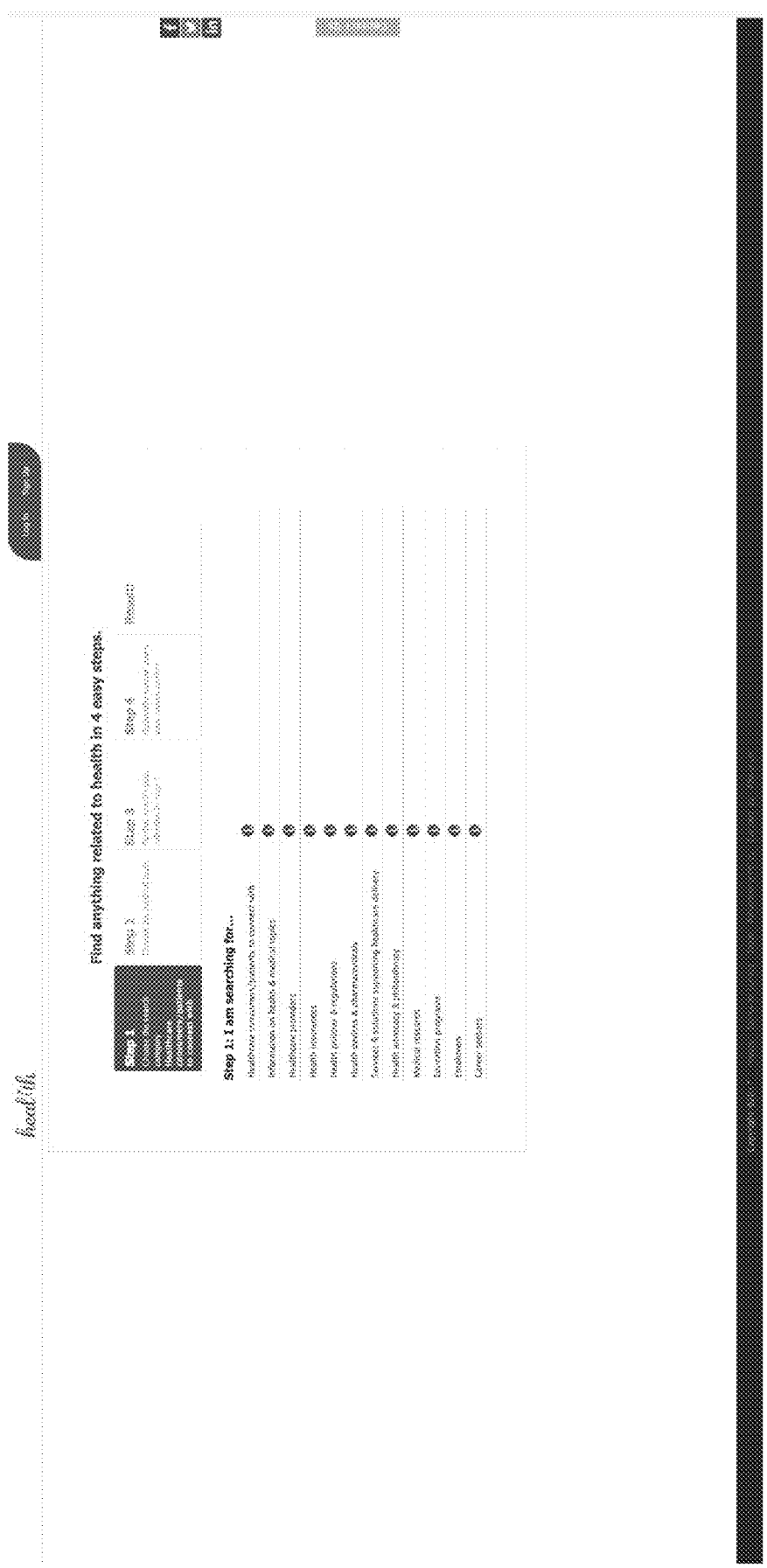
FIGS. 6-8 are screenshots of an online interface that allow for a user to select information using the classification code system to obtain medical and healthcare information.
Figure 7:
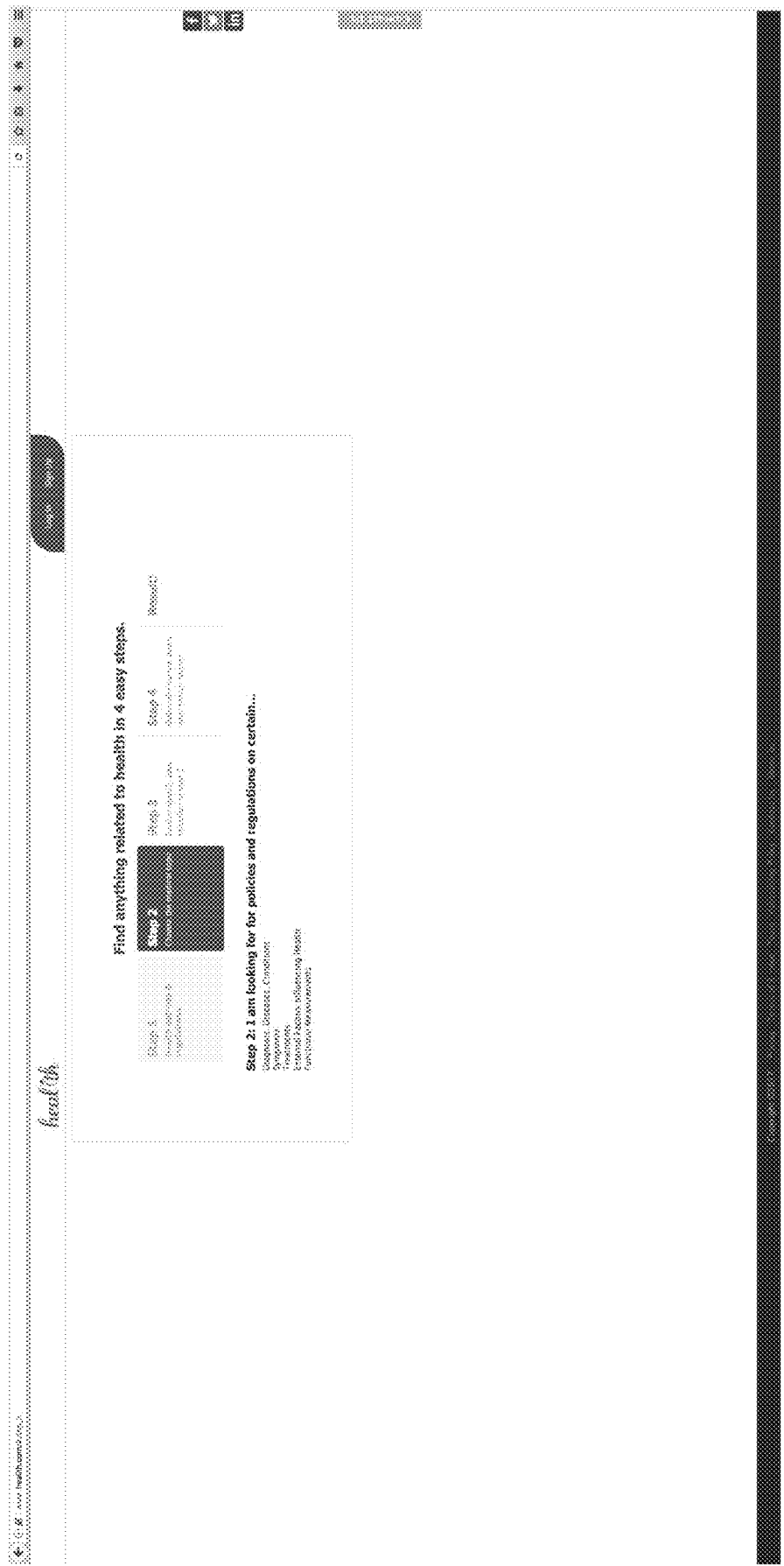
Figure 8:
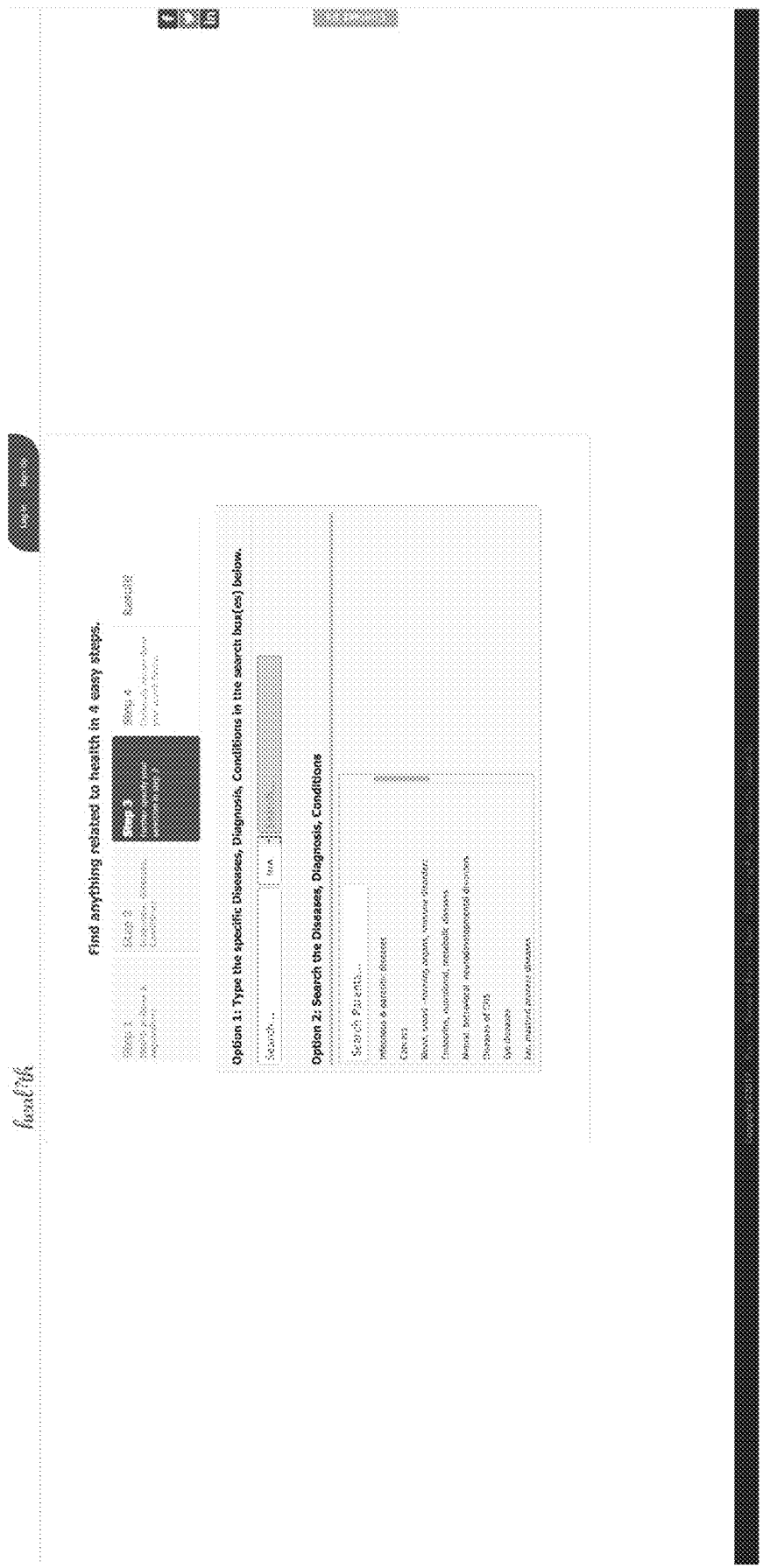

FIG. 5 conceptually illustrates a computer system with which some embodiments of the invention are implemented. The computer system 2100 includes a bus 2105, a processor 2110, a system memory 2115, a read-only memory 2120, a permanent storage device 2125, input devices 2130, and output devices 2135. In some embodiments, the computer system also includes a graphic processing unit (GPU) 2175.

The bus 2105 collectively represents all system, peripheral, and chipset buses that support communication among internal devices of the computer system 2100. For instance, the bus 2105 communicatively connects the processor 2110 with the read-only memory 2120, the system memory 2115, and the permanent storage device 2125.

From these various memory units, the processor 2110 (also referred to as central processing unit or CPU) retrieves instructions to execute and data to process in order to execute the processes of the invention. The read-only-memory (ROM) 2120 stores static data and instructions that are needed by the processor 2110 and other modules of the computer system.

The permanent storage device 2125, on the other hand, is a read-and-write memory device. This device is a non-volatile memory unit that stores instruction and data even when the computer system 2100 is off. Some embodiments of the invention use a mass-storage device (such as a magnetic or optical disk and its corresponding disk drive) as the permanent storage device 2125. The permanent storage device 2125 may be a fully solid-state storage, a conventional "spinning magnetic pallet" storage (i.e. hard-drive), or combinations thereof.

Other embodiments may use a removable storage device (such as a USB flash drive or SD Memory Card) as a temporary storage or as the permanent storage device 2125.

Like the permanent storage device 2125, the system memory 2115 is a read and write memory device. However, unlike storage device 2125, the system memory is a volatile read-and-write memory, such as a random-access memory. The system memory stores at least some of the instructions and data that the processor needs at runtime.

Instructions and/or data needed to perform processes of some embodiments are stored in the system memory 2115, the permanent storage device 2125, the read-only memory 2120, or any combination of the three. For example, the various memory units may contain instructions for processing multimedia items in accordance with some embodiments. From these various memory units, the processor 2110 retrieves instructions to execute and data to process in order to execute the processes of some embodiments.

The bus 2105 also connects to the input and output devices 2130 and 2135. The input devices enable the user to communicate information and select commands to the computer system. The input devices 2130 include alphanumeric keyboards, touch panels, and cursor controllers. The input devices 2130 also include scanners through which an image can be input to the computer system. The output devices 2135 display images generated by the computer system. The output devices may include printers, pen plotters, laser printers, ink-jet plotters, film recorders, and display devices, such as cathode ray tubes (CRT), liquid crystal displays (LCD), or electroluminescent displays.

As shown in FIG. 5, bus 2105 also couples computer 2100 to a network 2165 through a network adapter (not shown). In this manner, the computer can be a part of a network of computers (such as a local area network ("LAN"), a wide area network ("WAN"), or an Intranet) or a network of networks (such as the Internet). Finally, as shown in FIG. 4, the computer system in some embodiments also optionally includes a graphics processing unit (GPU) 2175. A GPU (also referred to as a visual processing unit or a display processor) is a dedicated graphics rendering device which is very efficient in manipulating and displaying computer graphics. The GPU can be included in a video card (not shown) or can be integrated into the mother board of the computer system along with the processor 2110. Also, the computer system 2100 may be used as a personal computer, a workstation, a game console, or the like. Any or all of the components of computer system 2100 may be used in conjunction with the invention. However, one of ordinary skill in the art will appreciate that any other system configuration may also be used in conjunction with the invention.

Having thus described several embodiments for practicing the inventive method, its advantages and objectives can be easily understood. Variations from the description above may and can be made by one skilled in the art without departing from the scope of the invention.

Accordingly, this invention is not to be limited by the embodiments as described, which are given by way of example only and not by way of limitation.

The invention claimed is:

1. A computerized method for associating non-scientific medical and healthcare common condition terms with medical classification system codes, comprising:

providing a database storing healthcare information including one or more classification system codes and one or more member profiles;

providing a processor;

providing one or more user interfaces allowing for user-defined inputs including one or more non-scientific medical and healthcare common condition terms to be entered by a user;

retrieving, via said processor, the healthcare information on said database;

correlating, via said processor, the one or more non-scientific medical and healthcare common condition terms entered via the one or more interfaces with the one or more medical classification system codes stored in the database;

updating the database with the correlated the one or more common conditions and the one or more medical and healthcare classification system codes; and sending, via said processor, said stored healthcare information from said database to the one or more user interfaces in response to user-defined inputs that include the one or more non-scientific medical and healthcare common condition terms, thereby allowing for a user-defined input that includes the one or more non-scientific medical and healthcare common condition terms to retrieve stored healthcare information related to the one or more medical classification system codes, wherein the classification system codes include global and national medical classifications such as World Health Organization system codes and any adaptations thereof.

2. The method of claim 1, wherein the one or more non-scientific medical and healthcare common condition terms are correlated with medical terms, formal terms, and one or more profiles with said stored healthcare information.

3. The method of claim 1, wherein the collected and stored healthcare information includes information relating to one or more of diseases, conditions, symptoms, abnormal findings, complaints, social circumstances, treatments, functional measurements, and external causes of injuries and/or diseases.

4. The method of claim 1, wherein each of the members inputs the stored healthcare information via a profile specific questionnaire.

5. The method of claim 1, wherein the profiles include one or more of consumers, providers, insurers, policy and regulatory, products and devices, services and solutions, advocacy and philanthropy, research, education, and employment.

6. The method of claim 1, wherein the classification system codes are CMS codes or WHO codes.

7. The method of claim 1 wherein the classification system codes are globally and/ or nationally recognized classification systems related to health and healthcare concatenated with their common medical terms.

8. The method of claim 1, wherein the classification system codes are updated based on the latest version of the globally and/or nationally recognized system codes they are based on.

9. The method of claim 1, wherein the non-scientific medical and healthcare common condition terms are suggested by users to the classification system codes and the classification system codes are updated upon administrative approval in the database.

10. The method of claim 1, wherein the search results are generated in response to a user-defined input.

11. The method of claim 1, wherein the user-defined input includes one or more of classification system codes, profiles, keywords, and area codes.

12. The method of claim 1, further comprising directing the user to one or more member websites.

13. The method of claim 1, further comprising facilitating communications between users and members.

14. A system for associating non-scientific medical and healthcare common condition terms with medical classification system codes, comprising:

a database storing healthcare information including one or more classification system codes and one or more member profiles, wherein healthcare information includes one or more classification system codes and one or more member profiles;

at least one processor;

one or more user interfaces allowing for user-defined inputs including one or more non-scientific medical and healthcare common condition terms to be entered by a user;

software executing on the processor configured to:
control access of said healthcare information;
correlate the one or more common medical terms with one or more non-scientific medical classification system codes, wherein the correlation between the non-scientific medical and healthcare common condition terms and the one or more classification system codes allows said healthcare information to be retrieved; and retrieve the stored healthcare information from the database in response to the user-defined inputs that include the non-scientific medical and healthcare one or more common condition terms and update the databased with the correlated the one or more common conditions and the one or more medical classification system codes, send said stored healthcare information from said database to the one or more user interfaces in response to user-defined inputs that include the one or more non-scientific medical common condition terms, thereby allowing for a user-defined input that includes the one or more non-scientific medical and healthcare common condition terms to retrieve stored healthcare information related to the one or more medical classification system codes, wherein the classification system codes include global and national medical classifications such as World Health Organization system codes and any adaptations thereof.

15. A method for associating non-scientific medical and healthcare common condition terms with medical classification system codes the method comprising the steps of:

providing an automated data processing system including a processor, software, and a storage including healthcare information data including one or more classification system codes and one or more member profiles;

providing a display, keyboard, and mouse in communication with the processor for interfacing with a system user;

providing an internet network connection in communication with the processor;

executing the software on the processor for the system user to input user profile data using the display, keyboard, and mouse;

executing the software on the processor for searching for and collecting healthcare information data based at least in part on the input user profile data using the internet network connection;

wherein the user profile data includes at least one non-scientific medical common language medical term relating to one or more disease, condition, symptom, abnormal finding, complaint, social circumstance, treatment, functional measurement, and external causes of injury;

correlating, via said processor, by executing the software on the processor user profile data with the collected healthcare information data;

retrieving and transmitting, via said processor, the healthcare information data to the storage corresponding to user profile data;

correlating by executing the software on the processor user profile data with the at least one non-scientific medical common language medical term;

correlating, via said processor, by executing software on the processor and using the internet network connection the user profile data including the at least one non-scientific medical common language medical term with one or more universally used healthcare classification code;

performing a recurring updated healthcare information data search and collection based at least in part on updated user profile data, at least in part on previous search and collection data, and at least in part on subsequent retrieving of updated healthcare information data to the storage;

updating the storage with the correlated the one or more common conditions and the one or more medical classification system codes;

sending, via said processor, said stored healthcare information from said database to the one or more user interfaces in response to user-defined inputs that include the one or more non-scientific medical common condition terms, thereby allowing for a user-defined input that includes the one or more non-scientific medical and healthcare common condition terms to retrieve stored healthcare information related to the one or more medical classification system codes; and presenting on the display recurrently updated healthcare information data corresponding to user profile data, wherein the classification system codes include global and national medical classifications such as World Health Organization system codes and any adaptations thereof.

* * * * *